United States Patent
Martinell et al.

(10) Patent No.: US 8,592,212 B2
(45) Date of Patent: *Nov. 26, 2013

(54) SOYBEAN TRANSFORMATION METHOD

(75) Inventors: Brian J. Martinell, Mt. Horeb, WI (US);
Lori S. Julson, Lake Mills, WI (US);
Carol A. Emler, Mt. Horeb, WI (US);
Yong Huang, Madison, WI (US);
Dennis E. McCabe, Middleton, WI
(US); Edward J. Williams, Madison, WI
(US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/245,599

(22) Filed: Sep. 26, 2011

(65) Prior Publication Data

US 2012/0096594 A1    Apr. 19, 2012

Related U.S. Application Data

(62) Division of application No. 12/291,576, filed on Nov. 12, 2008, now Pat. No. 8,030,076, which is a division of application No. 11/267,628, filed on Nov. 4, 2005, now abandoned, which is a division of application No. 10/029,374, filed on Dec. 20, 2001, now Pat. No. 7,002,058, which is a division of application No. 09/483,472, filed on Jan. 14, 2000, now Pat. No. 6,384,301.

(60) Provisional application No. 60/115,833, filed on Jan. 14, 1999.

(51) Int. Cl.
*C12N 15/84* (2006.01)
*C12N 15/82* (2006.01)

(52) U.S. Cl.
USPC .................................. 435/469; 800/278

(58) Field of Classification Search
None
See application file for complete search history.

(56) References Cited

U.S. PATENT DOCUMENTS

| | | | |
|---|---|---|---|
| 5,169,770 A | 12/1992 | Chee et al. | |
| 5,286,635 A * | 2/1994 | Hanson et al. | 800/294 |
| 5,463,175 A * | 10/1995 | Barry et al. | 800/300 |
| 5,565,346 A | 10/1996 | Facciotti et al. | |
| 5,633,435 A * | 5/1997 | Barry et al. | 800/288 |
| 5,693,512 A | 12/1997 | Finer et al. | |
| 5,824,877 A | 10/1998 | Hinchee et al. | |
| 5,914,451 A | 6/1999 | Martinell et al. | |
| 6,384,301 B1 * | 5/2002 | Martinell et al. | 800/294 |
| 7,002,058 B2 * | 2/2006 | Martinell et al. | 800/294 |
| 8,030,076 B2 * | 10/2011 | Martinell et al. | 435/469 |

FOREIGN PATENT DOCUMENTS

| | | |
|---|---|---|
| EP | 0 444 882 A2 | 4/1991 |
| WO | WO 94 02620 A | 2/1994 |

OTHER PUBLICATIONS

Chee et al. 1989, Plant Physiol. 91:1212-1218.*
Chee, Paula P., et al., "Transformation of soybean (*Glycine max*) via *Agrobacterium tumefaciens* and analysis of transformed plants," *Methods in Molecular Biology*, vol. 44 (K.M.A. Gartland and M. R. Davey, eds.), Totowa, New Jersey: Humana Press, 1995, ch. 11, pp. 101-119.
Chee, Paula P., et al., Transformation of soybean (*Glycine max*) by infecting germinating seeds with *Agrobacterium tumefaciens*, *Plant Physiology* 91:1212-1218 (1989).
Malone-Schoneberg, JoBeth, et al., Stable transformation of sunflower using *Agrobacterium* and split embryonic axis explants, *Plant Science* 103(2):199-207 (1994).
Trick, Harold N., et al., SAAT: Sonication-assisted *Agrobacterium*-mediated transformation, *Transgenic Research* 6(5):329-336 (1997).

* cited by examiner

*Primary Examiner* — Li Zheng
(74) *Attorney, Agent, or Firm* — Winston & Strawn LLP

(57) ABSTRACT

A method is disclosed for the *Agrobacterium*-mediated germline genetic transformation of soybean. The method is based on *Agrobacterium*-mediated gene delivery to individual cells in a freshly germinated soybean meristem, which cells can be induced directly to form shoots that give rise to transgenic plants. This method does not involve callus-phase tissue culture and is rapid and efficient.

6 Claims, No Drawings

SOYBEAN TRANSFORMATION METHOD

CROSS-REFERENCES TO RELATED APPLICATIONS

This application is a divisional of application Ser. No. 12/291,576 filed Nov. 12, 2008, issued U.S. Pat. No. 8,030,076, which is a divisional of application Ser. No. 11/267,628, filed Nov. 4, 2005, now abandoned, which claims priority to U.S. patent application Ser. No. 10/029,374, filed Dec. 20, 2001, now U.S. Pat. No. 7,002,058, which is a divisional of U.S. patent application Ser. No. 09/483,472, filed Jan. 14, 2000, now U.S. Pat. No. 6,384,301, which claims the benefit of U.S. provisional application No. 60/115,833, filed Jan. 14, 1999, all of which are incorporated by reference in their entirety.

FIELD OF THE INVENTION

The present invention relates to plant cell transformation and regeneration into a differentiated transformed plant. More particularly, the invention relates to a method for transforming soybean (*Glycine max*) using *Agrobacterium*-mediated transformation of a plant tissue explant and subsequent regeneration of the transformed cells into a whole plant.

BACKGROUND OF THE INVENTION

Cultivated soybean (*Glycine max*) has a substantial commercial value throughout the world. Over 50 million hectares worldwide are used to produce an annual crop of soybeans in excess of 100 metric tons with an estimated value exceeding 20 billion dollars. The development of scientific methods useful in improving the quantity and quality of this crop is, therefore, of significant commercial interest.

Modern biotechnological research and development has provided useful techniques for the improvement of agricultural products by plant genetic engineering. Plant genetic engineering involves the transfer of a desired gene or genes into the inheritable germline of crop plants such that those genes can be bred into or among the elite varieties used in modern agriculture. Gene transfer techniques allow the development of new classes of elite crop varieties with improved disease resistance, herbicide tolerance, and increased nutritional value. Various methods have been developed for transferring genes into plant tissues including high velocity microprojection, microinjection, electroporation, direct DNA uptake, and *Agrobacterium*-mediated gene transformation.

*Agrobacterium*-mediated gene transformation is the most widely used gene transfer technique in plants. This technique takes advantage of the pathogenicity of the soil dwelling bacteria, *Agrobacterium tumefaciens* or *Agrobacterium rhizogenes*. *Agrobacterium tumefaciens* natively has the ability to transfer a portion of its DNA, called T-DNA, into the genome of the cells of a plant to induce those cells to produce metabolites useful for the bacterium's nutrition. *Agrobacterium*-mediated transformation takes advantage of this concept by replacing the T-DNA of an *Agrobacterium* with a foreign set of genes, thus, making the bacterium a vector capable of transferring the foreign genes into the genome of the plant cell. Typically, the foreign gene construct that is transferred into the plant cell involves a specific gene of interest, which is desired to be introduced into the germline of the plant, coupled with a selectable marker that confers upon the plant cell a resistance to a chemical selection agent. Typically, the *Agrobacterium*-mediated gene transfer is into an undifferentiated cell cultivated in tissue culture, known as a callus cell, or the transfer is made into a differentiated plant cell from a leaf or stem, which is then induced to become an undifferentiated callus culture.

Although significant advances have been made in the field of *Agrobacterium*-mediated transformation methods, a need continues to exist for improved methods to facilitate the ease, speed and efficiency of such methods for transformation of soybean plants.

SUMMARY OF THE INVENTION

The present invention provides a novel and efficient method of performing germline transformation of soybean using *Agrobacterium*-mediated transformation directly on meristematic cells of soybean embryos. Direct shoot induction from transformed meristematic cells results in germline transgenic plants. The overall process is rapid and efficient.

One significant aspect of this invention is that the reduction of the pretreatment period of soybean seeds has improved the shoot production in surviving explants as well as reduced the time taken to produce plants that are transferable to a greenhouse. Also, the reduction of time and materials provides a system that is economically beneficial to those who implement it.

It is an object of the invention to provide a rapid and efficient method to perform soybean genetic transformation using *Agrobacterium*-mediated gene transfer.

It is another object of the present invention to provide a soybean transformation method not requiring a step of callus culture so that the method can be used on any soybean variety.

Another aspect of the present invention is to provide novel methods of wounding to increase transformation efficiency. One method of wounding involved exposing soybean embryos to ultrasonic sound waves (i.e., sonication). Another method involves wounding via a plasma blast of an electric gene gun.

Other objects, advantages, and features of the present invention will become apparent from the following specification.

DETAILED DESCRIPTION OF THE INVENTION

The present invention is a method for the direct germline genetic transformation of varieties of soybean, *Glycine max*. This method is based on *Agrobacterium*-mediated gene delivery into individual soybean cells in the meristem of a soybean embryo. The transformed cells are then induced to form shoots that are, at a high frequency, germline soybean transformants that can be cultivated into whole sexually mature and fertile transgenic soybean plants. The method does not involve a phase of callus culture, and hence the time period of the entire process from seed to transgenic seed is remarkably concise.

The method described here is based on *Agrobacterium*-mediated gene delivery into growing cells in an embryonic meristem. *Agrobacterium*-mediated techniques typically only result in gene delivery into one, or only a few, cells in the targeted tissue. Typically, a selective agent is applied post-transformation to kill all of the cells in the targeted tissues that are not transformed or to identify transformed cells through a selective advantage. Then a callus or other proliferative growth of transformed cells can be grown from which plants can be ultimately regenerated.

The method described here does not utilize a callus or proliferative phase. Instead, the *Agrobacterium*-mediated gene delivery is made into cells in the living meristem of a soybean embryo excised from a soybean seed. Then the meristematic region is cultured in the presence of a selection agent and a hormone to induce direct shoot formation. Preferably, the meristem is cultivated in the presence of the herbicide glyphosate, which acts both as a selection agent as well as a shoot-inducing hormone. The result of this step is the termination or at least growth retardation of most of the cells into which the foreign genetic construction has not been delivered and the simultaneous induction of the formation of soybean shoots, which arise from a small cluster of cells including a transformed meristematic cell. The meristem can also be cultivated in the presence of a selection agent, including, but not limited to, kanamycin.

This method is cultivar independent. The soybean tissue manipulations in this process are analogous to those in prior particle-mediated transformation methods, which have proven to be adaptable to all tested elite soybean varieties. This method is equally adapted for direct genetic transformation into elite soybean cultivars, thus potentially avoiding the need for extensive cross-breeding between varieties.

The time period required for this method is greatly reduced compared to other Agrobacterium-mediated transformation protocols. The soybean embryos are exposed to Agrobacterium transformation as soon as 6-14 hours after seed imbibition, are co-cultured for one to four days, and are then subjected to post-transformation selection. Viable phenotypically positive soybean shoots can be collected 3 to 6 weeks from the initiation of the procedure. The entire R0 (primary transformant) plant life cycle is not greatly longer than the minimum required for a soybean plant to grow to maturity in a greenhouse.

As with other Agrobacterium-mediated methods, the foreign genetic construction, or transgene, to be inserted into the soybean genome is created in vitro by normal techniques of recombinant DNA manipulations. The genetic construct is then transformed into the Agrobacterium strain for delivery into the soybean cells. The Agrobacterium is non-oncogenic, and several such strains are now widely available. The foreign genetic construction includes a selectable marker gene. Several such selectable marker genes are known, such as the gene for neomycin phosphotransferase II (NPT II), which expresses an enzyme conferring resistance to the antibiotic kanamycin and the related antibiotics neomycin, paromomycin, gentamicin, and G418. However, a preferred type of selectable marker gene is one of the genes conferring resistance to the herbicide glyphosate, such as the EPSP synthase gene described in U.S. Pat. No. 5,633,435 or the glyphosate oxidoreductase gene described in U.S. Pat. No. 5,463,175.

The starting material for the transformation process is a soybean seed. The seed is first soaked for softening and then induced to initiate germination. The seeds are imbibed in water for approximately 3 minutes and then allowed to soften for up to 2 hours. The softening step is not required for every seed lot. High quality seeds need less softening than low quality seeds. The softening step is to help keep the meristem intact. The seeds are then put on germination media and permitted to begin germination for a time period of about 6-24 hours, preferably for about 6-14 hours, and most preferably for about 8-12 hours.

Then the embryo is excised from the seed, and any primary leaf tissues are removed to expose the meristem of the soybean embryo.

For Agrobacterium-mediated gene transfer, wounding of the plant tissue is known to facilitate gene transfer. Therefore it is preferred, but not necessary, that the embryonic meristem is wounded at this step of the process. Many methods of wounding can be used, including, for example, cutting, abrading, piercing, poking, penetration with fine particles or pressurized fluids, plasma wounding, application of hyperbaric pressure, or sonication. Wounding can be performed using objects such as, but not limited to, scalpels, scissors, needles, abrasive objects, airbrush, particles, electric gene guns, or sound waves. Another alternative is vacuum infiltration. The procedure to this point will have typically taken 12-14 hours.

Preferably the wounding is done by sonication or plasma blast wounding. Sonication can be done in a bath sonicator or with a probe sonicator. A wetting agent, such as, but not limited to, Triton X-100 may or may not be used. Sonication can be done for between about 5 sec and about 10 min, preferably between about 5 seconds and about 40 seconds. Sonication is preferably done in the presence of the Agrobacterium.

Plasma blast wounding is done using an electric gene gun. Embryos are placed from 3-6 cm, preferably about 4 cm from the exposed electrodes, with 10 µL of water between them. A Plexiglass dome is then placed over the chamber and a partial vacuum is applied concurrent with an influx of helium gas. A minimum of about 16,000 volts is discharged through the water, vaporizing the water, and creating a plasma and shock wave engulfing the embryos. The embryos are then placed into the Agrobacterium culture.

The explants are then inoculated with the Agrobacterium culture for a few minutes to a few hours, typically about 0.5-3 hours. The excess media is drained and the Agrobacterium are permitted to co-cultivate with the meristem tissue for several days, typically three days in the dark. During this step, the Agrobacterium transfers the foreign genetic construct into some cells in the soybean meristem.

Next the explants are transferred to a medium containing the selection agent and appropriate antibiotics. This step is intended to terminate or at least retard the growth of the non-transformed cells and kill the remaining Agrobacterium cells. The length of culture depends, in part, on the toxicity of the selection agent to untransformed cells. For glyphosate selection, a two-day culture is effective, but the length of this culture step is variable, extending from one to seven days. For kanamycin selection, the explants are cultured from one to seven days.

Following this step, the meristems are placed in a medium conducive to shoot development for 3-7 days. The MSR medium used in the examples below contains benzylaminopurine (BAP), a shoot-inducing hormone. Glyphosate itself has also been found to induce shoot formation in soybean. The term hormone also includes cell growth regulating compounds that induce shoot formation, including, but not limited to, IAA, NAA, IBA, cytokinins, auxins, kinetins, glyphosate, and thiadiazorun. Whichever hormonal treatment is used, the individual transformed cells in a meristem give rise to transgenic sectors of tissue that are incorporated to a varying extent into the shoot arising directly from the explant. After culture on the MSR medium, the explants are transferred to WPM-BAP (a medium suitable for shoot development) for 4-5 weeks.

The elongated shoots are ready for harvest 3-6 weeks after the start of the entire transformation process. The shoots are evaluated for phenotypic regularity and health, and only shoots with elongated stems (approximately 1 inch) and full trifoliate leaf formation are harvested. The collected shoots are placed on a rooting medium to induce root formation. Root formation takes approximately 1-4 weeks, following which the plants can be transferred to soil and grown to full maturity. Ideally, the rooting medium also contains the selection agent, to help to terminate any non-transformants.

The R0 plants created by this technique are transgenic plants and are regularly recovered with quite reasonable yields. The number of independent germline plant lines recovered is usually in the single digit percentage number range. Thus, a repeat of this procedure on 100 planted soybean meristems would typically yield 1-10 independent lines of transgenic soybean.

EXAMPLES

The following examples further illustrate the present invention. They are in no way to be construed as a limitation in scope and meaning of the claims.

Methods and Materials

Media Preparation

Media used in the *Agrobacterium*-mediated transformation protocol employed to develop transformed soybean plants were prepared using standard methods known to one skilled in the art. Media formulations may be found in the cited references or in the Media Table (Table 3) that follows these examples.

Agrobacterium Preparation

*Agrobacterium tumefaciens* transformation vectors were constructed using standard molecular techniques known to those skilled in the art. These examples used the plasmid constructs pMON21112, containing both the FMV CP4syn gene and the e35s GUS gene; pMON15737, containing FMV GUS, NOS NPTII, and FMV CP4syn; pMON36133, containing e35S NPTII, GFP; and pMON36152, containing e35S cre, FMV CP4. The FMV CP4 gene used in constructing the plasmids is the promoter from Figwort Mosaic Virus (FMV) followed by the CP4syn gene, a synthetic gene encoding CP4 EPSP synthase. See, U.S. Pat. No. 5,633,435, which is incorporated by reference herein. EPSP synthase, when expressed, confers a substantial degree of glyphosate resistance upon the plant cell and plants generated therefrom. The e35s GUS gene is a β-glucuronidase gene, which is typically used as a histochemical marker, behind the e35S promoter. The FMV GUS gene is the FMV promoter with GUS. The NOS NPTII gene is a neomycin phosphotransferase gene, which confers resistance to kanamycin, behind the promoter for the nopaline synthase gene (NOS). GFP is the gene for green fluorescence protein, which is a selectable marker. Overnight cultures of *Agrobacterium* strain containing the plasmid used were grown to log phase and then diluted to a final optical density of 0.3 to 0.6.

Example 1

Transformation and Regeneration of Explants

Soybean seeds of cultivar A5403 were surface sterilized for three minutes in 50% clorox. Seeds were germinated in liquid bean germinating media (BGM) at a depth of two times the depth of the beans and incubated overnight at 20° C. dark. The composition of BGM is provided in the Media Table (Table 3).

Seed axis were prepared by removing the seed coat, breaking off the cotyledons and carefully removing primary leaf tissue to expose the meristematic region. Explants were then plated on OR media perpendicular to the surface with meristems away from the media and stored at 15° C. dark overnight. OR is a MS medium as modified by Barwale et al. (*Plants* 167:473-481, 1986) plus 3 mg/L BAP, 200 mg/L Carbenicillin, 62.5 mg/L Cefotaxime, and 60 mg/L Benomyl.

The next day explants were prepared for inoculation. Non-wounded explants were placed directly into the *Agrobacterium tumefaciens* inoculum. Wounded explants, those with damage to the meristematic tissue, were wounded by blasting with gold particles, scoring with a scalpel blade, poking, sonication, or piercing with fine needles. Vacuum infiltration was used in addition to and as an alternative to other wounding techniques. After one hour in inoculum, explants were placed with meristems facing down on plates containing filter paper and 3-10 mL of standard co-culture media (1/10 B5 medium [Gamborg et al., *Exp. Cell Res.*, 50:151-158, 1968]). Plates were incubated in the dark at room temperature for three days.

After the transformation culture, explants were transferred to liquid OR media containing 0.2 mM glyphosate and incubated for three days in the dark at 23-28° C. Following this stage, explants are removed from OR+0.2 mM glyphosate media and transferred to MSR+0.2 mM glyphosate and incubated in the dark at 28° C. for seven days. MSR media is MS media as listed above modified to include 0.4 mg/L BAP and 0.04 mg/L IBA (indole 3-butyric acid). Then explants were transferred to plantcons (small plastic containers used to culture small plants) containing woody plant medium (WPM) (McCown & Lloyd, *Proc. International Plant Propagation Soc.*, 30:421, 1981) minus BAP+0.075 mM glyphosate and incubated in the light in growth rooms at 28° C. with a 16-hour light/8-hour dark photoperiod. This step induced shoot formation, and shoots were observed from some cultured explants at this stage. Typically, explants were transferred to fresh WPM medium every two weeks until harvest was complete.

After five to six weeks, the explants had grown such that phenotype positive shoots could be pulled and rooted. These plants were then sent to the greenhouse to grow out and for further analysis.

Transformation Efficiency

Glyphosate selection indicated a transformation efficiency rate of 1-3%. Transformation efficiency was determined by comparing the number of phenotypically normal plants that survived the selection protocol with the number of explants initially prepared and inoculated. Table 1 summarizes the data on transformation efficiency. All plants indicated as germline positive correctly passed the transgenes on to their progeny by Mendelian inheritance.

TABLE 1

*AGROBACTERIUM* TRANSFORMATION OF MERISTEMS
Construct pMON21112(FMV CP4, e35s GUS), Cultivar A5403

| Experiment | No. of Explants | Explant Preparation | Inoculation | Total Shoots Sent to GH | Total CP4 + Shoots | Total Germline to Date (Apr. 20, 1998) | Germline T.E. |
|---|---|---|---|---|---|---|---|
| 58.1 | 100 | Bombarded | Vacuum Infiltrate | 3 | 3 | 2/3 | 2% |

TABLE 1-continued

*AGROBACTERIUM* TRANSFORMATION OF MERISTEMS
Construct pMON21112(FMV CP4, e35s GUS), Cultivar A5403

| Experiment | No. of Explants | Explant Preparation | Inoculation | Total Shoots Sent to GH | Total CP4 + Shoots | Total Germline to Date (Apr. 20, 1998) | Germline T.E. |
|---|---|---|---|---|---|---|---|
| 58.2 | 100 | Scored | Standard (no vacuum) | 1 | 0 | 0/1 | 0% |
| 58.3 | 100 | Scored | Standard | 4 | 4 | 2/4 | 2% |
| 58.4 | 100 | Pierced | Standard | 1 | 1 | 1 | 1% |
| 58.5 | 100 | Pierced | Vacuum | 2 | 2 | 2/2 | 2% |
| 138.8 | 80 | Pierced | Standard | 1 | n/a | 1/1 | 1.2% |

Example 2

Soybean seeds of cultivar A4922 were soaked in sterile distilled water for three minutes at room temperature then drained and left moist for two hours with periodic rolling. After two hours, the seeds were placed in BGM medium to twice the depth of the seeds, and the seeds were incubated at room temperature in the dark.

At twelve hours from initiation of germination, the seed axes were removed from the seeds and placed in sterile distilled water for holding. The meristems were then wounded by puncturing with a needle, the wounding being repeated at all three meristems in each seed axis, the primary and the two secondary meristems associated with each axillary leaf primordia. The meristems were then inoculated with induced *Agrobacterium* culture carrying the transgene, approximately 12-14 hours after initiation of the germination. After two hours, the meristems were drained and placed in co-culture medium for three days of co-cultivation in the dark.

At day 4, the explants were placed in a petri dish with BGM, swirled and shaken for 1 to 2 hours with changes of BGM medium. Then the explants were plated on OR medium with 0.075 mM glyphosate and cultured in the dark at room temperature for two days.

At day 6 the explants were transferred to MSR medium with 0.075 mM glyphosate and cultured in the dark for three days at room temperature.

At day 9, the explants were transferred to plantcons containing WPM minus BAP but with 0.075 mM glyphosate for shooting and were incubated in the light at 28° C. The shoots that appeared were cut from the meristems from which they arose after 4 to 5 weeks. The shoots were, rooted and cultivated to maturity in a greenhouse.

Out of the original 170 explants subjected to this procedure, eight phenotypically positive plants that were glyphosate resistant were recovered. Analysis of RI data confirms the presence of the inserted transgenes.

Example 3

Sonication Wounding and Kanamycin Selection

Soybean seeds are soaked in sterile distilled water for three minutes at room temperature, drained, and left moist for two hours. BGM medium is added after two hours to 2-3 times the depth of the seed volume and incubated at room temperature in the dark for six to eleven hours.

At eight to thirteen hours from initiation of germination, the seed axes are removed from seeds and held in sterile distilled water. Explants are rinsed with sterile distilled water, drained and divided into sets of 50-300. Sets are placed into a vessel along with *Agrobacteria* (induced or not induced) and can also include a wetting agent. Examples of vessels include a 25 mL glass test tube along with 2 mL of *Agrobacterium* or a 125 mL glass flask with 5-10 mL *Agrobacterium*.

Each vessel is then held in a sonicator with 500-1000 mL of distilled water in the bath +/−0.1% Triton X-100 and sonicated for 5-30 seconds in the test tubes or for 20-40 seconds in the flask. Total inoculation time ranges from five minutes to three hours +/−fresh *Agrobacterium*, +/−vacuum infiltration pulled multiple times or held at 25 inches Hg or shaking at 0-120 RPM on an orbital shaker.

Explants are then co-cultured on one filter paper with one to seven milliliters of 1/10 B5 medium for two to four days at 23° C. in the dark. Following co-culture, explants can be rinsed with BGM and shaken on an orbital shaker for two hours to reduce bacterial load before transferring to the next stage.

Selection of transformed shoots is obtained through the use of kanamycin or glyphosate.

Kanamycin Selection

Either kanamycin sulfate or kanamycin nitrate may be used. After co-culture, explants are then transferred to solid OR media plus 0 to 300 ppm kanamycin for one to seven days at 23° C., dark. Explants are then transferred to WPM media minus BAP containing 50 to 300 ppm kanamycin and placed at 28° C., 16 hours light/8 hours dark photoperiod. Subcultures to WPM media with the same concentration of kanamycin or higher are made one to three weeks later.

Shoots are pulled between three and six weeks post-inoculation. Shoots are rooted on BRM with 0 to 175 ppm kanamycin.

Glyphosate Selection

After co-culture, explants are transferred either to OR, OR/MSR, or directly to WPM media plus 0 to 2000 μM glyphosate. Explants can spend two to seven days on OR media or two to five days on OR plus two to seven days on MSR media. Explants are then transferred to WPM minus BAP. In some cases a fresh transfer to the same media is made after two weeks.

Shoots are pulled between three and six weeks post-inoculation. Shoots are rooted on BRM (see Table 3) with 0 to 40 μM glyphosate.

Germlines are confirmed by testing leaf tissue of R1 plants by GUS assay, NPTII ELISA, CP4 ELISA, or PCR.

Table 2 shows transformation results for three different constructs and three soybean varieties utilizing either kanamycin or glyphosate selection after sonication or poke wounding. Germline efficiencies (Total number of explants/Total number of germline transformants) range from 0.5% to 3.3%.

TABLE 2

Agrobacterium Transformation Using Sonication and Poke Wounding Utilizing Glyphosate or Kanamycin Selection

| Experiment | Construct | Variety | No. of Explants | Sonication Duration (sec) | Inoculation (hours) | Selection | No. of Germlines | Germline TE |
|---|---|---|---|---|---|---|---|---|
| 4.2 | pMON36133 | A4922 | 106 | 30 | 1 | kanamycin (SO4) | 1 | 0.9% |
| 60.6 | pMON36133 | A4922 | 33 | 5 | 1 + vacuum | kanamycin (SO4) | 1 | 3.0% |
| 60.7 | pMON36133 | A4922 | 30 | 30 | 1 + vacuum | kanamycin (SO4) | 1 | 3.3% |
| 92.5 | pMON15737 | A3244 | 92 | 15 | 1 + vacuum | kanamycin (NO3) | 1 | 1.1% |
| 123.1 | pMON15737 | A3469 | 200 | poked* | 1.25 | kanamycin (NO3) | 1 | 0.5% |
| 123.2 | pMON15737 | A3469 | 183 | poked | 1.25 + vacuum | kanamycin (NO3) | 1 | 0.5% |
| 11.1 | pMON36152 | A4922 | 62 | 15 | 1 | glyphosate | 1 | 1.6% |
| 39.1 | pMON36152 | A4922 | 38 | 15 | 3 | glyphosate | 1 | 2.6% |
| 68.1 | pMON36152 | A4922 | 105 | 15 | 1.5 | glyphosate | 2 | 1.9% |
| 70.2 | pMON15737 | A4922 | 107 | 15 | 1.25 + vacuum | glyphosate | 1 | 0.9% |
| 81.2 | pMON15737 | A4922 | 113 | 15 | 1.75 + vacuum | glyphosate | 1 | 0.9% |

Constructs:
pMON15737 (FMV:GUS; NOS:NPTII; FMV:CP4syn)
pMON36133 (e35s:lox:modified NPTII:lox:GFP)
pMON36152 (e35s:cre; FMV:arab EPSP TP:CP4 EPSPS)
*poked = single stab to center of all three maristems using a 4 flat shader tattoo needle Example 4

Plasma Blast Wounding

Soybeans were germinated for 14 hours as described in Example 2. Wounding was done by suspending the embryos 4 cm from the exposed electrodes of the electric gene gun. Discharge was set to 16,000 volts. A partial vacuum under helium gas was established in the blast chamber. The embryos were engulfed in the plasma and shock wave upon discharging the voltage through a 10 µL water droplet bridging the electrodes.

After wounding, embryos were incubated with *Agrobacterium* inoculum containing pMON15737 for 1.5 hours and selected with glyphosate as described in Example 2. Of the seven targets of 12 embryos for the control group, one phenotypic shoot was observed and did not root on glyphosate rooting medium. Of the seven targets of 12 embryos for the treatment group, three phenotypic shoots were observed, one of these rooted and was sent to the greenhouse. It tested positive for GUS expression in the vascular tissue, which indicates germline transformation, and had GUS positive seed, confirming transformation at the R1 generation.

TABLE 3

MEDIA

BEAN GERMINATION MEDIA (BGM 2.5%)

| COMPOUND: | QUANTITY PER LITER |
|---|---|
| BT STOCK #1 | 10 mL |
| BT STOCK #2 | 10 mL |
| BT STOCK #3 | 3 mL |
| BT STOCK #4 | 3 mL |
| BT STOCK #5 | 1 mL |
| SUCROSE | 25 g |
| Adjust to pH 5.8. | |

DISPENSED N 1 LITER MEDIA BOTTLES, AUTOCLAVED

| ADDITIONS PRIOR TO USE: | PER 1 L |
|---|---|
| CEFOTAXIME (50 mg/mL) | 2.5 mL |
| FUNGICIDE STOCK | 3 mL |

BT Stock for Bean Germination Medium
Make and store each stock individually. Dissolve each chemical thoroughly in the order listed before adding the next. Adjust volume of each stock accordingly. Store at 4° C.

Bt Stock 1 (1 Liter)

| $KNO_3$ | 50.5 g |
|---|---|
| $NH_4NO_3$ | 24.0 g |
| $MgSO_4 * 7H_2O$ | 49.3 g |
| $KH_2PO_4$ | 2.7 g |

Bt Stock 2 (1 Liter)

| $CaCl_2 * 2H_2O$ | 17.6 g |
|---|---|

Bt Stock 3 (1 Liter)

| $H_3BO_3$ | 0.62 g |
|---|---|
| $MnSO_4\_H_2O$ | 1.69 g |
| $ZnSO_4—7H_2O$ | 0.86 g |
| KI | 0.083 g |
| $NaMoO_4—2H_2O$ | 0.072 g |
| $CuSO_4—5H_2O$ | 0.25 mL of 1.0 mg/mL stock |
| $CoCl_4—6H_2O$ | 0.25 mL of 1.0 mg/mL stock |

Bt Stock 4 (1 Liter)

| $Na_2EDTA$ | 1.116 g |
|---|---|
| $FeSO_47H_2O$ | 0.834 g |

Bt Stock 5 (500 mL) Store in a Foil Wrapped Container

| Thiamine-HCl | 0.67 g |
|---|---|
| Nicotinic Acid | 0.25 g |
| Pyridoxine-HCl | 0.41 g |

BRM Media Stock (for 4 L)

| MS Salts | 8.6 g |
|---|---|
| Myo-Inositol (Cell Culture Grade) | .40 g |

-continued

| | |
|---|---|
| Soybean Rooting Media Vitamin Stock | 8 mL |
| L-Cysteine (10 mg/mL) | 40 mL |
| Sucrose (Ultra Pure) | 120 g |
| | pH 5.8 |
| Washed Agar | 32 g |

Additions after Autoclaving:

| | |
|---|---|
| BRM/TSG Hormone Stock | 20.0 mL |
| Ticarcillin clavulanic acid (100 mg/mL Ticarcillin) | 4.0 mL |

Soy Tissue Culture Hormone Pre-Mixes
MSR Pre-Mixed Hormones
Use 10.0 mL per liter
Store dark at 4° C.

| Amount for 1 liter | Amount for 20 liters |
|---|---|
| 0.80 mL BAP (0.5 mg/mL) | 16.0 mL BAP (0.5 mg/mL) |
| 0.040 mL IBA (1.0 mg/mL) | 0.80 mL IBA (1.0 mg/mL) |
| 9.16 mL SDW (sterile distilled water) | 183.2 mL SDW |

OR Pre-Mixed Hormones
Use 10.0 mL per liter. Store dark at 4° C.

| Amount for 1 liter | Amount for 30 liters |
|---|---|
| 6.0 mL BAP (0.5 mg/mL) | 180.0 mL BAP (0.5 mg/mL) |
| 0.037 mL NAA (1.0 mg/mL) | 1.11 mL NAA (1.0 mg/mL) |
| 3.96 mL SDW | 118.8 mL SDW |

WPM Pre-Mixed Hormones
Use 10.0 mL per liter

| Amount for 1 liter | Amount for 50 liters |
|---|---|
| 0.080 mL BAP (0.5 mg/mL) | 4.0 mL BAP (0.5 mg/mL) |
| 9.92 mL SDW | 496.0 mL SDW |
| Store dark at 4° C. | |

BRM/TSG Hormone Stock

| Amount for I1 liter | Amount for 40 liters |
|---|---|
| 6.0 mL IAA (0.033 mg/mL) | 240.0 mL IAA (0.033 mg/mL) |
| 4.0 mL SDW | 160.0 mL SDW |
| Store dark at 4° C. | |

Vitamin Stock for Soybean Rooting Media (1 Liter)

| | |
|---|---|
| Glycine | 1.0 g |
| Nicotinic Acid | 0.25 g |
| Pyridoxine HCl | 0.25 g |
| Thiamine HCl | 0.05 g |

Dissolve one ingredient at a time, bring to volume, store in foil-covered bottle in refrigerator for no more than one month.

3× Minor MS Salts Stock (1 Liter)

| | |
|---|---|
| $H_3BO_3$ | 1.86 g |
| $MnSO_4$—$H_2O$ | 5.07 g |
| $ZnSO_4$—$7H_2O$ | 2.58 g |
| KI | 0.249 g |
| $NaMoO$—$2H_2O$ | 0.075 g |
| $CuSO_4$—$5H_2O$ Stock (1.0 mg/mL) | 7.5 µL |
| $CoCl_2$—$6H_2O$ Stock (1.0 mg/mL) | 7.5 µL |

Dissolve one chemical at a time, adjust volume, store in refrigerator.

Fungicide Stock (100 mL)

| | |
|---|---|
| chlorothalonile (75% WP) | 1.0 g |
| benomyl (50% WP) | 1.0 g |
| captan (50% WP) | 1.0 g |

Add to 100 mL of sterile distilled water.
Shake well before using.
Store 4° C. dark for no more than one week.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method of germline transforming and culturing a soybean plant cell using Agrobacterium mediation, the method comprising:
    (a) initiating the germination of a soybean seed;
    (b) isolating the embryonic axis including the embryonic meristem from the soybean seed to prepare an explant;
    (c) wounding the explant;
    (d) exposing the explant to a disarmed Agrobacterium vector comprising a heterologous genetic construct comprising a selectable marker gene wherein the heterologous genetic construct is transferred into at least one cell in the explant; and
    (e) culturing the explant in the presence of a selection agent in a manner allowing identification of soybean cells of the explant to which the heterologous genetic construct has been transferred and in the presence of a shoot inducing agent, wherein the selection agent is glyphosate and the shoot inducing agent is only glyphosate.

2. The method of claim 1, wherein the selectable marker gene is an EPSPS synthase gene or a glyphosate oxidoreductase gene.

3. The method of claim 2, wherein the EPSPS synthase gene is CP4 EPSPS synthase.

4. The method of claim 3, wherein said CP4 EPSPS synthase gene is CP4syn gene.

5. The method of claim 1, wherein the wounding is caused by ultrasonic waves, by a plasma blast discharge, or by puncturing the soybean explant with a needle, other sharp object, or an abrasive object.

6. A method of producing a fertile transgenic soybean plant comprising:
   (a) producing a soybean cell according to the method of claim 1; and
   (b) cultivating a transgenic soybean plant from said cell.

* * * * *